United States Patent [19]

Trova

[11] Patent Number: 5,470,979

[45] Date of Patent: Nov. 28, 1995

[54] ASYMMETRIC SYNTHESIS OF BICYCLIC AMINO ACID ESTERS

[75] Inventor: Michael P. Trova, Salisbury Mills, N.Y.

[73] Assignee: American Cyanamid Company, Wayne, N.J.

[21] Appl. No.: 270,199

[22] Filed: Jul. 1, 1994

[51] Int. Cl.⁶ .................................................. C07D 217/26
[52] U.S. Cl. .......................................... 546/147; 546/146
[58] Field of Search ..................................... 546/146, 147

[56] References Cited

U.S. PATENT DOCUMENTS 5,430,150  7/1995  Trova ..................................... 546/199

FOREIGN PATENT DOCUMENTS 432694  6/1991  European Pat. Off. .
432695  6/1991  European Pat. Off. .

OTHER PUBLICATIONS

J. Med. Chem. 1994, 37, pp. 1177–1188—The Development of Cyclic Sulfolanes as Novel and High–Affinity $P_2$ Ligands for HIV–1 Protease Inhibitors.

Tetrahedron Letters, vol. 32, No. 3, pp. 327–330, 1991—Peptide Ester Hydrolysis Knestle, Karen L. et. al.

Tetrahedron Letters: Asymmetry, vol. 2, No. 12, pp. 1262–1282, 1991—Asymmetric Synthesis of Pipecolic Acid Derivatives Using the Aza–Diels–Alder Reaction–Balley Patrick D. et al.

Tetahedron: Assymetry vol. 3 No. 4 pp. 459–505 1992.

Hook; Synthetic Communications, 1984 14 pp. 83–87.

Tetrahedron vol. 48, No. 44, pp. 9707–9718, 1992—Reaction D'Aza–Diels–Alder Diastereoselective.

J. Chem. Soc. Perkin Trans. 1991–pp. 1337–1340–Enantio–and Diastereo–Selective Synthesis of Pipecolic Acid Derivatives using the Aza–Diels–Alder Reaction of Imines with Dienes.

Liebigs Ann. Chem. 1991–pp. 1045–1048–Asymmetric Synthesis of Bicyclic Amino Acid Derivatives by Aza–Diels–Alder Reactions in Aqueous Solution–H. Waldmann and Matthias Braun.

J. Med. Chem. 1993, 36, pp. 2046–2048–A Structurally novel, Systemically Active, Competitive AMPA Receptor Antagonist–P. L. Ornstein et al.

Drug Design for Neuroscience, edited by Alan P. Kozikowski, Raven Press, Ltd. N.Y. 1993–pp. 258–309–Design and Synthesis of Conformationally Constrained Acidic Amino Acids as N–Methyl–D–Aspartic Acid Receptor Antagonists–Paul L. Ornstein.

Tetrahedron Letters 1993 34 pp. 2593–2596.

Drugs of the Future, 1991, 16(3): pp. 210–212–Ro 31–8959/003–Aniviral.

Org. Synth, 1987, 65, 90–97–A General Synthetic Method for the Preparation of Conjugated Dienes from Olefins using Bromomethanesulfonyl Bromide: 1, 2–Dimethylenecyclohexane.

Tetrahadron Letters, vol. 31, No. 18, pp. 2603–2606, 1990–Asymmetric AZA–Diels–Alder Reaction Using the Chiral 1–Phenyl–Ethyl Imine of Methyl Glyoxylate[1]–L. Stella, H. Abraham.

Primary Examiner—Bernard Denta
Attorney, Agent, or Firm—T. S. Szaltkowski

[57] ABSTRACT

The invention is an improved process for producing an optically active compound of formula IV:

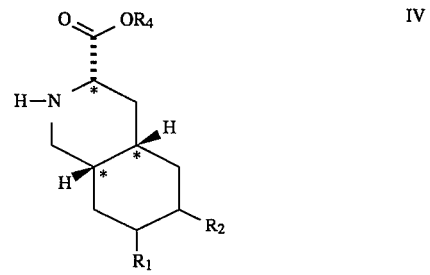

wherein $R_1$, $R_2$ and $R_4$ are herein described.

The improved process to produce a compound of formula IV comprises:
a). reacting a diene with a chiral compound, containing a chiral auxiliary to obtain an olefinic compound;
b). removing the chiral auxiliary and reducing the olefin by hydrogenation to obtain a compound of formula IV.

20 Claims, No Drawings

5,470,979

ASYMMETRIC SYNTHESIS OF BICYCLIC AMINO ACID ESTERS

BACKGROUND OF THE INVENTION

1. Field of the Invention

The invention relates to an improved process for producing optically active bicyclic amino acid ester compounds which compounds are useful as intermediates for the synthesis of other compounds useful as inhibitors of retroviral protease enzymes and antagonists of the excitatory amino acid (EAA) receptor.

SUMMARY OF THE INVENTION

The invention provides an improved process for producing an optically active compound of formula IV:

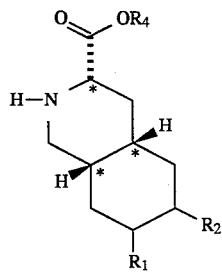

wherein:

$R_1$ and $R_2$ may be the same or different and are selected from H; straight or branched $(C_1-C_5)$alkyl; phenyl; and $-(CH_2)_nOSi(R_3)_3$ wherein n=0–2 and $R_3$ may be the same or different and is selected from $(C_4-C_5)$alkyl and phenyl; and $R_4$ is $(C_1-C_4)$alkyl.

The improved process to produce a compound of formula IV comprises:

a) reacting a compound of formula I:

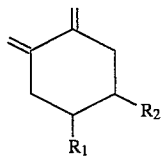

wherein:

$R_1$ and $R_2$ may be the same or different and are selected from H; straight or branched $(C_1-C_5)$alkyl; phenyl; and $-(CH_2)_nOSi(R_3)_3$ wherein n=0–2 and $R_3$ may be the same or different and is selected from $(C_4-C_5)$ alkyl and phenyl; with a chiral compound of formula II, which contains a chiral auxiliary:

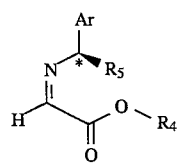

wherein:

$R_4$ is $(C_1-C_4)$alkyl;
$R_5$ is a straight or branched $(C_1-C_4)$alkyl;
and Ar is phenyl; substituted phenyl wherein the substituents are selected from $(C_1-C_4)$ alkoxide, $(C_1-C_5)$alkyl, nitro and phenyl; naphthyl; or substituted naphthyl wherein the substituents are selected from $(C_1-C_4)$ alkoxide, $(C_1-C_5)$ alkyl, and phenyl; in an inert solvent with an acid catalyst and a catalytic amount of water; to obtain a compound of formula III:

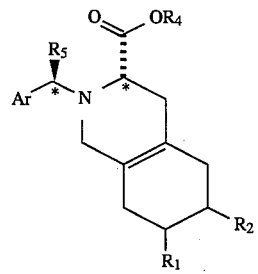

wherein $R_1$, $R_2$, $R_4$, $R_5$ and Ar are as defined hereinabove;

b) removing, from the compound of formula III, the chiral auxiliary, and reducing the olefin by hydrogenation using a transition metal catalyst; and obtaining a compound of formula IV:

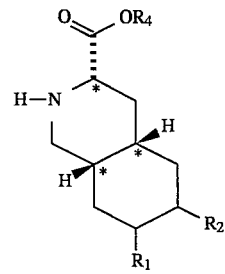

wherein $R_1$, $R_2$, and $R_4$, are as defined hereinabove.

Also included in the present invention are novel compounds useful as intermediates in the novel process of the present invention. Such novel intermediates include those of formula III:

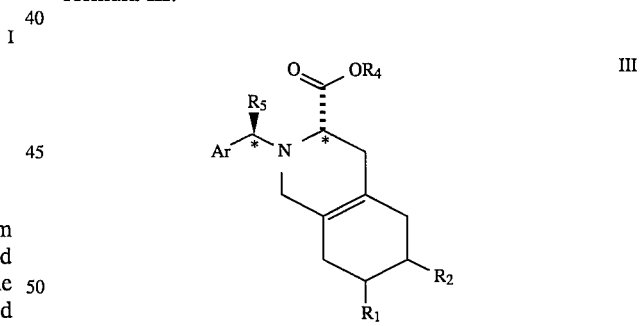

wherein $R_1$ and $R_2$ may be the same or different and are selected from H; straight or branched $(C_1-C_5)$ alkyl; phenyl; and $-(CH_2)_nOSi(R_3)_3$ wherein n=0–2 and $R_3$ may be the same or different and is selected from $(C_4-C_5)$ alkyl and phenyl;

$R_4$ is $(C_1-C_4)$ alkyl;

$R_5$ is straight or branched $(C_1-C_4)$ alkyl; and

Ar is phenyl; substituted phenyl wherein the substituents are selected from $(C_1-C_4)$ alkoxide, $(C_1-C_5)$ alkyl, nitro and phenyl; naphthyl; or substituted naphthyl wherein the substituents are selected from $(C_1-C_4)$ alkoxide, $(C_1-C_5)$ alkyl, and phenyl.

Additionally, according to the present invention, the compound of formula IV:

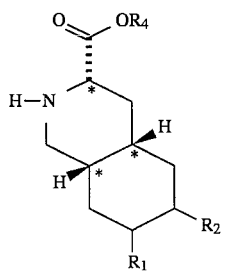

IV wherein
$R_1$, $R_2$ and $R_4$ are as defined hereinabove; may be further reacted under hydrolysis conditions: room temperature with an alkali or alkaline earth carbonate in an aqueous alcohol solution; to give a compound of formula V:

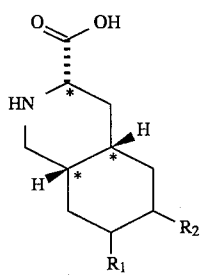

V wherein $R_1$ and $R_2$ are as defined hereinabove.

Additionally, according to the present invention the compound of formula IV:

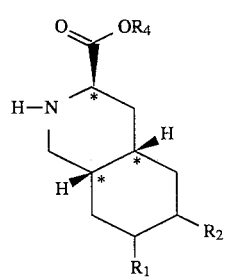

IV wherein $R_1$, $R_2$ and $R_4$ are as defined hereinabove; may be further reacted, in an inert solvent at room temperature, with (isobutyl)$_2$AlNHC(R$_6$)$_3$ wherein $R_6$ is a straight or branched ($C_1$-$C_4$) alkyl; to give a compound of the formula VI:

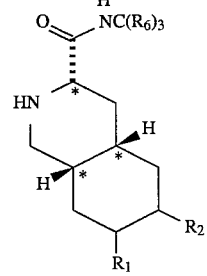

VI wherein $R_1$, $R_2$, and $R_6$ are as defined hereinabove.

The compounds of formula V and VI are compounds which are useful as further intermediates for the synthesis of inhibitors of retroviral protease enzymes and antagonists of the excitatory amino acid (EAA) receptor.

DESCRIPTION OF THE PREFERRED EMBODIMENT

According to Scheme 1, 1,2-dimethylenecyclohexane 1, readily prepared by literature methods (Block, E., et al, *Org. Syn.*, 1987, 65, 90–97) is allowed to react at room temperature with [(R)-(1-phenylethyl)imino] acetic acid ethyl ester 2, prepared by literature methods (Bailey, P., et al, *Tetrahedron: Asymmetry*, Vol. 2, No. 12, p 1263–1282, 1991), in dimethylformamide (DMF) solution, in the presence of trifluoroacetic acid (TFA) and a catalytic amount of water, to provide as a Diels-Alder product compound 3 and minor isomer 7. The isomers, 3 and 7, are separated by column chromatography [Silica Gel: 2X: 1st column eluted with 10% ethyl acetate/hexane; 2nd column eluted with 0.4% ethyl acetate/hexane]. It is contemplated that ethyl alcohol may be used as a reaction solvent. It is further contemplated that acids other than TFA may be used in this synthetic step to catalyze the reaction, for example hydrochloric acid. A catalytic amount of water is required for the reaction to proceed in good yield. In the instance when DMF is used as a solvent, the catalytic amount of water required is 0.01 equivalents. An alternative Diels-Alder protocol may be utilized as described in Tetrahedron Letters, Vol. 31, No. 18, 2603–2606, 1990.

The olefin, located within the octahydroisoquinoline ring system, and the nitrogen benzyl-protecting group of 3 are removed by catalytic hydrogenation with a transition metal catalyst at 15–40 psi of hydrogen gas to provide 4. The catalyst used is Pearlman's catalyst,

SCHEME 1

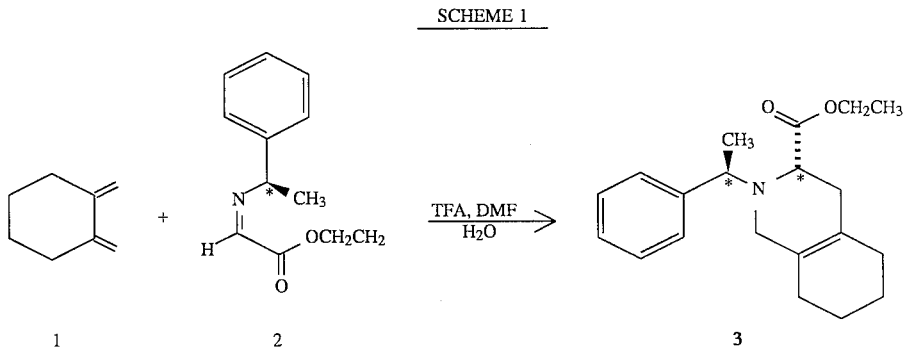

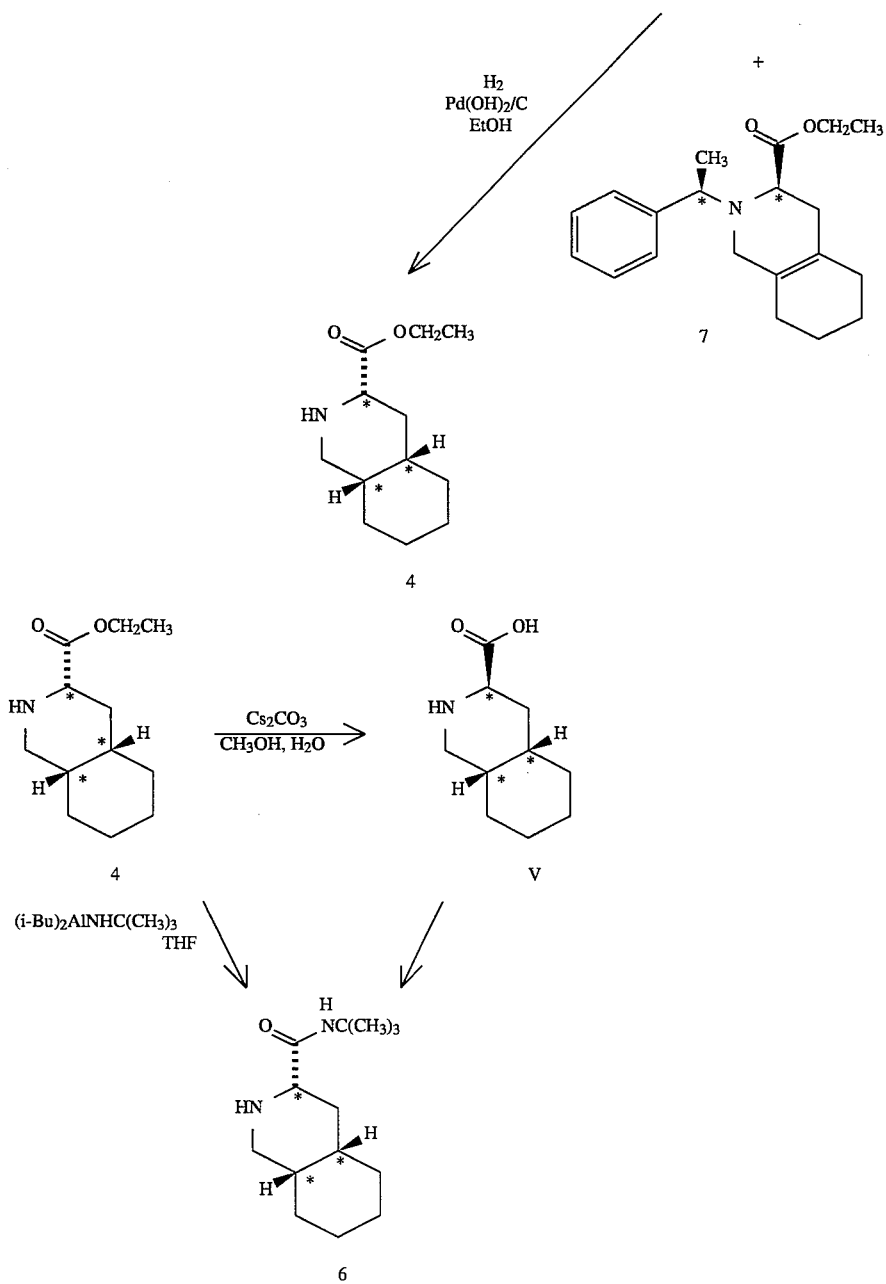

Pd(OH)$_2$/C, in ethyl alcohol solution. It is contemplated that transition metal catalysts other than Pearlman's catalyst may be used, for example rhodium-on-carbon.

The ethyl ester of 4 is hydrolyzed at room temperature to carboxylic acid 5 by reaction with cesium carbonate, Cs$_2$CO$_3$, in aqueous alcohol. It is contemplated that other alkaline earth carbonates may be equally effective in the saponification reaction, for example potassium carbonate, sodium carbonate or rubidium carbonate.

The ethyl ester 4 is converted to the tertbutylamide 6 at room temperature by reaction with diisobutylaluminum tert-butylamide, (isobutyl)$_2$AlNHC(R$_6$)$_3$ wherein R$_6$ is methyl; in an inert solvent following a related protocol described in the literature (*Tetrahedron Letters*, 1993, 34, 2593–2596).

Appropriate inert solvents are toluene and methylene chloride. Additionally, any (isobutyl)$_2$AlNHC (R$_6$)$_3$ wherein R$_6$ is a straight or branched (C$_1$–C$_4$) alkyl may also be used.

The isolated products of formula III through VI are purified by chromatography, distillation or recrystallization before being carried on to the next reaction step.

Compounds of formula IV(4), V(5), and VI(6) of the present invention are valuable intermediates useful in the synthesis of inhibitors of retroviral protease enzymes and in the synthesis of antagonists of the excitatory amino acid (EAA) receptor; examples of which are the ionotropic N-methyl-D-aspartic acid (NMDA) receptor and the 2-amino-3-(5-methyl-3-hydroxy-isoxazol-4-yl) propanoic acid (AMPA) receptor. The procedures used to synthesize antagonists of the excitatory amino acid receptor are found in *Drug Design for Neuroscience*, Chapter 11, P. L. Ornstein, pp 285–309, edited by A. P. Kozikowski, Raven Press, Ltd., N.Y., 1993, and in *J. Med. Chem.*, Ornstein, P. L. et al, 36, 2046–2048; the contents of which are incorporated herein by reference. Thus, these compounds are useful for the synthesis of agents to treat Huntington's Chorea, Atzheimer's disease, Parkinson's disease, cerebral ischemia and head trauma.

The compounds of formula IV(4), V(5) and VI(6) are valuable synthetic intermediates for the preparation of potent HIV-1 Protease inhibitors. HIV-1 Protease inhibitors are useful in the treatment of acquired immune deficiency syndrome (AIDS); See U.S. patent application Ser. No. 991,876 filed Dec. 16, 1992, now U.S. Pat. No. 5,430,150, EP 432694A2 and EP 432695 A2; the contents of which are incorporated by reference.

The present described process is an improvement over the literature and patent references.

The advantages include:

(1) no significant epimerization of any of the newly created asymmetric centers;

(2) permits the use of low pressure hydrogen, 15–40 psi, at ambient temperature;

(3) short, concise synthesis: only three steps from known diene 1 to acid 5; and (4) short, concise synthesis: only three steps from known diene 1 to amide 6.

It will be appreciated by those skilled in the art that the atoms labeled with an asterisk (*) represent an optically active asymmetric center.

Further, it will be appreciated by those skilled in the art that the use of the enantiomerically related chiral auxiliary of the present invention will result in the preparation of the enantiomerically related products. Contemplated chiral auxiliaries, as exemplified by d'Angelo et al, *Tetrahedron: Asymmetry*, Vol. 3, No. 4, 459–505, 1992, are illustrated below:

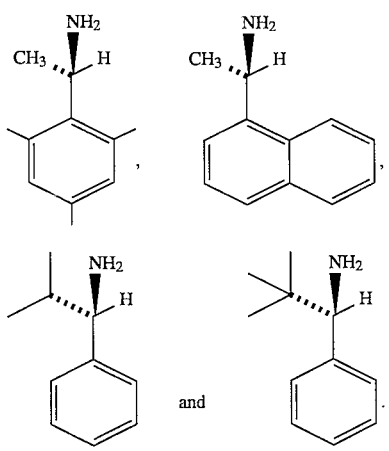

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Bromomethanesulfonyl Bromide

To a room temperature slurry of 100 g of symtrithiane and 685 ml of water is added, dropwise, 190 ml of bromine. To the reaction mixture is added, dropwise, 685 ml of water followed by 185 ml of additional bromine. After the completion of the addition, the reaction mixture is stirred for 30 minutes. The layers are separated and the aqueous layer is extracted 2X with methylene chloride. The combined organic layers are washed successively with cold 10% aqueous sodium metabisulfite, water and saturated sodium chloride, dried and concentrated in vacuo to give 249 g of the desired product.

$^1$H NMR(CDCl$_3$)δ: 5.04(s,2H).

Reference: Block, E., Aslam, M., *Org. Synth.*, 1987, 65, 90–97.

EXAMPLE 2

1-Bromo-1-methyl-2-(bromomethylsulfonyl) cyclohexane

Into each of six pyrex test tubes, cooled to 0° C., is placed 6.15 ml of 1-methylcyclohexene, 24 ml of dry methylene chloride and 13.61 g of product from Example 1. The six tubes are attached around a quartz photolysis immersion well, maintained at 0° C., and irradiated with a 450-Watt mercury lamp for 2 hours. Following the irradiation, 1.51 g of potassium carbonate is added to each test tube and the contents are filtered through a pad of anhydrous sodium sulfate. The filtrates are combined and concentrated in vacuo to give 88.5 g of the desired product.

$^1$H NMR(CDCl$_3$)δ: 4.58(AB quartet, 2H); 3.99(dd, 1H); 2.45–2.05 (m, 4H); 2.15 (s, 3H); 1.9–1.54 (m, 4H).

Reference: Block, E., Aslam, M., *Org. Synth.*, 1987, 65, 90–97.

EXAMPLE 3

1,2-Dimethylenecyclohexane

To a room temperature solution of 110.85 g of tert-butoxide in 667 ml of tert-butyl alcohol and 75 ml of tetrahydrofuran is added, dropwise, 100 g of product from Example 2 dissolved in 167 ml of tert-butyl alcohol and 19 ml of tetrahydrofuran. The reaction mixture is stirred for 1 hour at room temperature prior to being diluted with 500 ml of water and extracted with 4×300 ml of petroleum ether. The combined organic layers are washed with water, saturated sodium chloride, dried, and filtered. The filtrated is distilled at atmospheric pressure to remove the excess solvents. The residue is distilled at 55°–61° C. (100 mmHg) to give 14.0 g of the desired product as a colorless oil.

$^1$H NMR(CDCl$_3$)δ: 4.94–4.92(m,2H); 4.67–65(m,2H); 2.28–2.24 (m, 4H); 1.68–1.61 (m, 4H).

Reference: Block, E., Aslam, M., *Org. Synth.*, 1987, 65, 90–97.

EXAMPLE 4

Ethyl Glyoxylate

A solution of 47 ml of ethyl diethoxyacetate, 23.34 g of glyoxylic acid monohydrate and 0.5 g of p-toluenesulfonic acid monohydrate is heated at 100° C. for 17 hours. The reaction mixture is cooled to room temperature and 32 g of phosphorous pentoxide is added. The mixture is heated at 100° C. for 2 hours and then cooled to room temperature. The resulting syrup is distilled at 56°–60° C. (50 mmHg) to yield 42.06 g of the desired product as a colorless oil.

$^1$H NMR(CDCl$_3$)δ: 9.40(s,1H); 4.38(q,2H); 1.4(t,3H).

Reference: Hook, J., *Synth. Commun.*, 1984, 14, 83–87.

EXAMPLE 5

[(R) - (1-Phenylethyl) iminolacetic Acid Ethyl Ester

A solution of 5.0 g of product from Example 4, 5.93 g of (R)-(+)-α-methylbenzyl amine and 6.31 ml of toluene is heated at the reflux temperature for 1.5 hours. Water is removed from the reaction mixture during the heating with the aid of a Dean-Stark trap. The reaction mixture is cooled to room temperature and concentrated in vacuo to give 10.05 g of the desired product as an orange oil.

$^1$H NMR(CDCl$_3$)δ: 7.72(br s,1H); 7.36–7.33(m,5H); 4.6(q, 1H); 4.34(q,2H); 1.62(d,3H); 1.34(t,3H).

Reference: Bailey, P. D., Brown, G. R., Korber, F., Reed, A., Wilson, R. D., Tetrahedron: Asymmetry, 1991, 2, 1263–1282.

EXAMPLE 6

[R-(R*,S*)]-1,2,3,4,5,6.7,8-Octahydro-2-(1-phenylethyl)-3-isoquinoline Carboxylic Acid Ethyl Ester To a round-bottom flask charged with 3.16 g of product from Example 3 is added a solution of 2.0 g of product from Example 5 dissolved in 7 ml of N,N-dimethylformamide containing 751 µl of trifluoroacetic acid and 1.8 µl of water. The reaction mixture is stirred at room temperature for 84 hours. The solvent is removed under reduced pressure and the residue is dissolved in chloroform. The organic layer is washed with saturated aqueous sodium bicarbonate and saturated sodium chloride, dried over potassium carbonate, filtered and the solvents are removed in vacuo. The residue is purified by column chromatography (silica gel: 10% ethyl acetate/hexane) followed by further column chromatography (silica gel: 0.4% ethyl acetate/hexane) to give 0.919 g of the desired product as a colorless solid.

$[α]_{25°}{}^D$ 51.7 (c=1.43, methyl alcohol).

$^1$H NMR(CDCl$_3$)δ: 7.38–7.18(m,5H); 4.16(q,J=7.1 Hz,2H); 4.06–3.95(m,2H); 3.09–2.73(m,2H); 2.58–2.23(m,2H); 1.96–1.75 (m, 2H); 1.70–1.40 (m, 6H); 1.35 (d, J=6.6 Hz, 3H); 1.27 (t,J=7.1 Hz,3H).

$^{13}$C NMR (CDCl$_3$)δ: 173.40, 145.87, 128.17, 127.20, 126.86, 126.63, 123.56, 61.79, 59.74, 55.21, 51.06, 33.62, 29.39, 27.15, 22.84, 22.57, 20.74, 14.36 ppm.

IR(neat); 1722, 1195,cm$^{-1}$.

MS (FAB): m/e 314 (M+H).

Analysis Calculated for C$_{20}$H$_{27}$NO$_2$: C=76.64; H=8.68; N=4.47;

Found: C=76.37; H=8.51; N=4.43.

EXAMPLE 7

[3S- (3α, 4αβ, 8αβ)]-1,2,3,4,4a,5,6,7,8,8a-Decahydro-3-isoquinolinecarboxylic Acid Ethyl Ester A solution of 1.0 g of product from Example 6 dissolved in 53 ml of ethyl alcohol and 0.997 g of Pearlman's catalyst is hydrogenated in a Parr apparatus with 45 pounds per square inch (psi) of hydrogen for 45 hours. The catalyst is removed by filtration through a pad of diatomaceous earth and the filtrate is concentrated in vacuo to give 0.604 g of crude product. $^1$H NMR indicates the presence of a minor impurity, which is removed by column chromatography (silica gel: 5% methyl alcohol/chloroform) to give 0.303 g of the desired product as a colorless oil.

$[α]_{25°}{}^D$ –66.7 (c=0.61, methyl alcohol).

IR(neat): 2923, 2859, 1738, 1448 cm$^{-1}$.

$^1$H NMR(CDCl$_3$)δ: 4.18(q,J=7.1 Hz,2H); 3.34–3.29(m, 1H); 2.89–2.8(m,2H); 1.93–1.24(m,13H); 1.28(t,J=7.1 Hz,3H).

$^{13}$C NMR(CDCl$_3$)δ: 173.54, 60.51, 59.34, 51.30, 35.39, 34.38, 31.59, 29.30, 26.20, 24.82, 20.65, 14.07.

MS(FAB): m/e 212 (M+H).

Analysis Calculated for C$_{12}$H$_{21}$NO$_2$: C=68.21; H=10.02; N=6.63;

Found: C=68.50; H=10.29; N=6.56.

EXAMPLE 8

3R-(3α,4αβ,8αβ)-1,2,3,4,4a,5,6,7,8,8a-Decahydro-3-isoquinolinecarboxylic Acid

To a room temperature solution of 0.0723 g of product from Example 7 dissolved in 3.6 ml of methyl alcohol and 0.35 ml of water is added 0.223 g of cesium carbonate. The reaction mixture is stirred at room temperature for 18 hours, then diluted with chloroform and neutralized to pH 6.0 with 10% aqueous citric acid. The aqueous layer is further extracted 3X with chloroform, the organic layers are combined and concentrated in vacuo to give 0.612 g of the desired product as an ivory solid.

$[α]_{25°}{}^D$ –18.7(c=0.71, 0.1N hydrochloric acid/methyl alcohol).

$^1$H NMR(CD$_3$OD, CDCl$_3$)δ: 3.86–3.83 (m, 1H); 3.33 (s, 1H); 2.08–1.22 (m, 12H).

MS(FAB): m/e 184 (M+H).

EXAMPLE 9

3S-(3α,4αβ,8αβ)]-N-(1,1-Dimethylethyl)-1,2,3,4,4a,5,6,7,8,8a-decahydro-3-isoquinolinecarboxamide To room temperature solution of 0.149 ml of tert-butylamine dissolved in 3.5 ml of toluene and 3.5 ml of tetrahydrofuran, is added 1.42 ml of triisobutylaluminum (1.0M toluene solution). The solution is heated at 45° C. for 1 hour, cooled to room temperature, and concentrated in vacuo. The residue is resuspended in 5.0 ml of tetrahydrofuran and 0.10 g of product from Example 8 dissolved in 4 ml of tetrahydrofuran is added. The reaction is stirred at room temperature for 18 hours. The mixture is diluted with 10 ml of 10% aqueous tartaric acid disodium salt, extracted 5 times with ethyl acetate. The combined organic layers are washed with saturated sodium chloride, dried and concentrated in vacuo. The residue is purified by column chromatography (silica gel: 50% EtOAc, 49% hexane, 1% triethylamine) to give 0.0522 g of the desired product.

$^1$H NMR(CDCl$_3$)δ: 6.51 (brs, 1H); 3.08–3.00 (m, 1H); 2.84–2.80 (m, 2H); 1.90–1.25(m,13H); 1.37 (s,9H).

MS (FAB): m/e 239 (M+H).

I claim:
1. A process for producing a compound of formula IV:

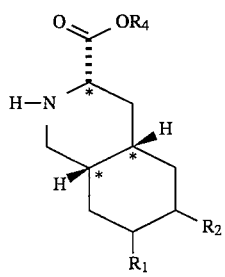

wherein:
$R_1$ and $R_2$ may be the same or different and are selected from H; straight or branched $(C_1-C_5)$alkyl; phenyl; and $—(CH_2)_n OSi(R_3)_3$, n=0-2, and $R_3$ may be the same or different and is selected from $(C_4-C_5)$alkyl and phenyl; and
$R_4$ is $(C_1-C_4)$ alkyl;
which comprises:
reacting a compound of formula I:

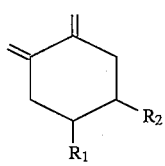

wherein:
$R_1$ and $R_2$ are as defined hereinabove;
with a chiral compound of formula II, which contains a chiral auxiliary;

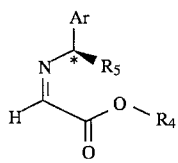

wherein:
$R_4$ is as defined hereinabove;
$R_5$ is a straight or branched $(C_1-C_4)$alkyl; and
Ar is phenyl; substituted phenyl wherein the substitutents are selected from $(C_1-C_4)$alkoxide, $(C_1-C_5)$ alkyl, nitro and phenyl; naphthyl; or substituted naphthyl wherein the substituents are selected from $(C_1-C_4)$alkoxide, $(C_1-C_5)$alkyl, and phenyl; in an inert solvent with an acid catalyst and a catalytic amount of water; and obtaining a compound of formula III:

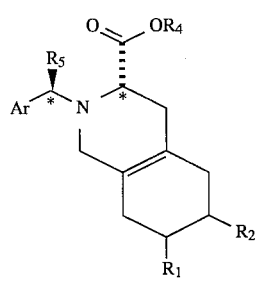

wherein $R_1$, $R_2$, $R_4$, $R_5$ and Ar are as defined hereinabove;
removing, from the compound of formula III, the chiral auxiliary and reducing the olefin by hydrogenation using a transition metal catalyst and thereby obtaining a compound of formula IV wherein $R_1$, $R_2$, $R_4$, and $R_5$ are as defined hereinabove.

2. A process according to claim 1 further comprising:
reacting a compound of formula IV:

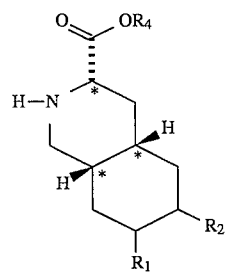

wherein
$R_1$ and $R_2$ may be the same or different and are selected from H; straight or branched $(C_1-C_5)$alkyl; phenyl; and $—(CH_2)_n OSi(R_3)_3$, n=0-2 and $R_3$ may be the same or different and is selected from $(C_4-C_5)$ alkyl and phenyl; and
$R_4$ is $(C_1-C_4)$alkyl;
under hydrolyzing conditions: room temperature with an alkali or alkaline earth carbonate in aqueous alcohol and obtaining a compound of formula V:

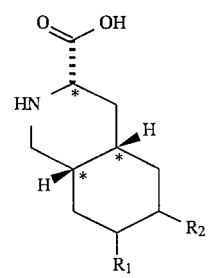

wherein $R_1$ and $R_2$ are as defined hereinabove.

3. A process according to claim 1 which further comprises:
reacting a compound of formula IV:

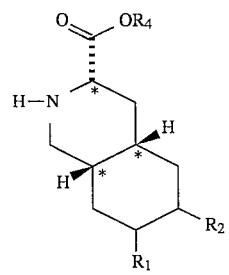

wherein
$R_1$ and $R_2$ may be the same or different and are selected from H; straight or branched $(C_1-C_5)$alkyl; phenyl; and $—(CH_2)_n OSi(R_3)_3$, n=0-2 and $R_3$ may be the same or different and is selected from $(C_4-C_5)$ alkyl and phenyl; and $R_4$ is $(C_1-C_4)$ alkyl;
with $(isobutyl)_2AlNHC(R_6)_3$, wherein $R_6$ is a straight or branched $(C_1-C_4)$ alkyl, in an inert solvent at room temperature; and thereby obtaining a compound of formula VI:

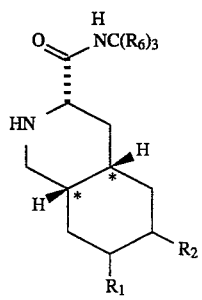

wherein:

$R_1$, $R_2$ and $R_6$ are as defined hereinabove.

4. The process of claim 1, wherein compound III is purified by chromatography, distillation or recrystallization.

5. The process of claim 1, wherein compound IV is purified by chromatography, distillation or recrystallization.

6. The process of claim 1 wherein said inert solvent comprises N,N-dimethylformamide or ethyl alcohol.

7. The process of claim 1 wherein said acid catalyst comprises trifluoroacetic acid or hydrochloric acid.

8. The process of claim 1 wherein said catalytic amount of water comprises 0.01 equivalent.

9. The process of claim 1 wherein said transition metal catalyst comprises Pearlman's catalyst or rhodium-on-carbon.

10. The process of claim 2, wherein compound V is purified by chromatography, distillation or recrystallization.

11. The process of claim 2, wherein said alkali or alkaline metal carbonate comprises cesium carbonate, potassium carbonate, sodium carbonate or rubidium carbonate.

12. The process of claim 3, wherein compound VI is purified by chromatography, distillation or recrystallization.

13. The process of claim 3 wherein said inert solvent comprises toluene or methylene chloride.

14. The process of claim 3 wherein said $R_6$ of (isobutyl)$_2$AlNHC($R_6$)$_3$ is methyl.

15. The process of claim 1; wherein the intermediate of formula III which is obtained is [R-(R*,S*)]-1,2,3,4,5,6,7,8-octahydro-2-(1-phenylethyl)-3-isoquinoline carboxylic acid ethyl ester.

16. The process of claim 1 wherein [3S-(3α,4αβ,8αβ)]-1,2,3,4,4a,5,6,7,8,8a-decahydro-3-isoquinolinecarboxylic acid ethyl ester is produced.

17. The process of claim 2 wherein 3S-(3α,4αβ,8αβ)]-1,2,3,4,4a,5,6,7,8,8a-decahydro-3-isoquinolinecarboxylic acid is produced.

18. The process of claim 3 wherein 3S-(3α,4αβ,8αβ)]-N-(1,1-dimethylethyl)-1,2,3,4,4a,5,6,7,8,8a-decahydro-3-isoquinolinecarboxamide is produced.

19. A compound of formula III:

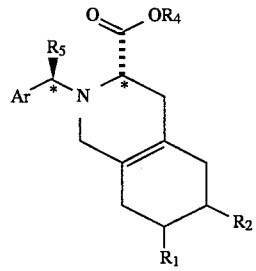

wherein $R_1$ and $R_2$ may be the same or different and are selected from H; straight or branched ($C_1$–$C_5$) alkyl; phenyl; and —(CH$_2$)$_n$ OSi ($R_3$)$_3$, n=0–2, and $R_3$ may be the same or different and is selected from ($C_4$–$C_5$) alkyl and phenyl;

$R_4$ is ($C_1$–$C_4$) alkyl;

$R_5$ is a straight or branched ($C_1$–$C_4$) alkyl; and

Ar is phenyl; substituted phenyl wherein the substitutents are selected from ($C_1$–$C_4$) alkoxide, ($C_1$–$C_5$) alkyl, nitro and phenyl; naphthyl; or substituted naphthyl wherein the substituents are selected from ($C_1$–$C_4$)alkoxide, ($C_1$–$C_5$)alkyl, and phenyl.

20. The compound according to claim 19, R-(R*, S*)]-1,2,3,4,5,6,7,8-octahydro-2-(1-phenylethyl)-3-isoquinoline carboxylic acid ethyl ester.

* * * * *